United States Patent [19]

Novotny et al.

[11] Patent Number: 5,074,982

[45] Date of Patent: Dec. 24, 1991

[54] SUPPRESSION OF ELECTROOSMOSIS WITH HYDROLYTICALLY STABLE COATINGS

[75] Inventors: Milos V. Novotny; Kelly A. Cobb, both of Bloomington, Ind.; Vladislav Dolnik, Brno, Czechoslovakia

[73] Assignee: Indiana University Foundation, Bloomington, Ind.

[21] Appl. No.: 603,589

[22] Filed: Oct. 26, 1990

[51] Int. Cl.$^5$ .......................... C25B 1/00; B01D 61/42
[52] U.S. Cl. .............................. 204/182.8; 204/180.1; 204/299 R
[58] Field of Search .............. 204/299 R, 182.8, 180.1

[56] References Cited

U.S. PATENT DOCUMENTS 4,680,201  7/1987  Hjerten ............................ 204/182.8
4,997,537  3/1991  Karger ............................ 204/299 R

OTHER PUBLICATIONS

Payne, "Simultaneous Deactivation and Coating of Porous Silica Particles for Microcolumn Supercritical Fluid Chrom.", Anal. Chem., 62, 1379–1384 (1990).
Burrows, "Thermostable deactivation reagents for capillary column preparation", Jour. of Chrom., 260, 168–172 (1983).

Primary Examiner—John Niebling
Assistant Examiner—Caroline Koestner
Attorney, Agent, or Firm—Townsend and Townsend

[57] ABSTRACT

Surfaces of silica-containing materials, such as the inner walls of silica capillaries, used in chromatographic, particularly electrophoretic, separations are coated with an organic polymer layer to reduce or eliminate surface charges. The layer is applied by first converting the silanol groups on the surface to silicon halide groups, then reacting these groups with an organometallic reagent having a terminal ethenyl moiety, preferably vinyl or allyl lithium or a vinyl or allyl magnesium halide, to convert the silicon halide groups to Si—R groups where the R retains the terminal ethenyl moiety, and finally reacting these ethenyl groups newly attached to the surface with a neutral organic monomer in an addition polymerization reaction to form a monomolecular noncrosslinked polymer layer over the surface. The resulting polymer layer is linked to the silica directly through a Si—C bond which is stable over a wide range of pH conditions.

6 Claims, 2 Drawing Sheets

SUPPRESSION OF ELECTROOSMOSIS WITH HYDROLYTICALLY STABLE COATINGS

The U.S. Government has a paid-up license in this invention and the right in limited circumstances to require the patent owner to license others on reasonable terms as provided for by the terms of Grant No. PHS R01 GM 24349 awarded by the National Institute of General Medical Sciences, U.S. Public Health Service.

This invention lies in the field of coated silica materials, with a focus on vessels, chambers and other structures used in electrophoresis.

BACKGROUND OF THE INVENTION

Solid elements serve a variety of functions in electrophoretic and chromatographic systems. In some systems, solid elements serve as sites for the partitioning of solutes, whereas in others they serve as retaining walls for housing separation media. Solid elements thus occur as particles, tubes and plates, depending on the separation mechanism to be employed as well as the arrangement, size and shape of the separation medium. Examples of separation systems using solid elements are affinity chromatography, reversed-phase chromatography, ion exchange chromatography, size exclusion chromatography, and the various forms of electrophoresis, including slab gel electrophoresis, tube gel electrophoresis, capillary electrophoresis (both gel and solution types), isotachophoresis and isoelectric focusing. In some cases, the solid element plays an active role in the partitioning, and in other cases, a passive role.

A phenomenon which occurs in many of these systems, particularly those in which the solid element is a silica-containing material, is electroendosmosis, also referred to as electroosmotic flow, which arises from an electrokinetic potential existing between the wall of the solid element and the liquid or gel separation medium adjacent to the wall. The flow which is caused by this potential is a bulk flow which occurs when an electric field tangential to the solid surface is imposed on the separation medium. In many systems, this bulk flow is considered an interference with the separation process.

While electroosmotic flow can occur in any of these configurations, it is particularly troublesome in capillaries due to their high ratio of wall surface area to internal volume, and to the close proximity of the wall to the sample components being separated. Capillaries are particularly significant since they permit the analysis of extremely small samples with on-line spectroscopic detection, as well as the use of high voltages, thereby achieving separations at high speed.

Accordingly, the suppression of electroosmotic flow in chromatographic, and particularly electrophoretic, systems is one of the goals addressed by the present invention.

Also addressed by this invention is a phenomenon encountered in the separation of proteins by such techniques. Proteins have an inherent tendency to adsorb to silica surfaces. In most separation processes, this adsorption is undesirable, since it leads to peak broadening and asymmetry, and is thereby detrimental to resolution, lowering the accuracy and reproducibility of analyses.

Protein adsorption is of particular concern in systems which are susceptible to electroosmotic flow, since the adsorbed protein affects the wall characteristics, including the zeta potential. Changes in the quantity or distribution of adsorbed protein on the wall will cause the electroosmotic contribution of the flow to vary, both within a single run and between successive runs, further aggravating the difficulties in performing reliable and meaningful comparisons and determinations. Again, these concerns are particularly acute in capillary systems, due to the capillary geometry and the high influence of the capillary wall.

Various methods of reducing or eliminating protein adsorption by silica surfaces are reported in the literature. In general, these methods involve one of two approaches:

(1) creating a Coulombic repulsion between the proteins and silica by appropriate selection of buffer pH and ionic strength; and (2) chemically bonding a neutral material to the silica surface to eliminate the surface charges which function as adsorption sites.

Examples of the first approach are reported by Mc-Cormick, R. M., *Anal. Chem.* 60:2322–2328 (1988), who describes the use of low pH phosphate buffers to reduce the negative charge of fused silica and distribute phosphate groups over the silica surface as a form of protective screening. The use of high pH buffers with added ionic modifiers is reported by Lauer, H. H., et al. *Anal. Chem.* 58:166–170 (1986), and Walbroehl, Y., et al., *J. Microcolumn Sep.* 1:41–45 (1989). As reported by these authors, the buffers convert the proteins to negatively charged species which are repelled by the negatively charged capillary walls.

The second approach was adopted by Jorgenson, J. W., et al., *Science* 222:266–272 (1983), Who bonded glycol-containing materials to fused silica. Hjertén, S. J., *J. Chromatogr.* 347:191–198 (1985) reported the use of methylcellulose and non-crosslinked polyacrylamide bonded through an organosilane reagent. The use of a poly(vinylpyrrolidinone) coating, applied by way of organosilane surface derivatization was reported by McCormick, referenced above, and the use of a polyethylene glycol coating is reported by Bruin, G. J. M. et al., *J. Chromatogr.* 471:429–436 (1989).

While each of these approaches has certain merits, they suffer disadvantages as well, particularly due to limits on their ranges of applicability. Approaches involving manipulation of buffer pH and ionic strength are limited in terms of the range of pH under which the separation can be performed, and hence the proteins which can be separated. Approaches involving coating of the silica surface encounter problems in long-term stability, particularly under alkaline conditions. The widely used technique of bonding through siloxane (Si—O—Si—C) bonds, for example, is prone to nucleophilic cleavage under basic conditions.

For protein separation, it is important that one be able to select from a wide range of buffers and pH values because of the vast differences among proteins and the strong influence of pH on the charges of protein molecules, and hence on their migration characteristics. Certain mixtures are best separated at low pH (below the isoelectric point of the proteins), while others afford better separations at pH values above the protein isoelectric points. The ideal system will therefore be one which is both stable and capable of use in both high and low pH regimes.

SUMMARY OF THE INVENTION

A novel method of suppressing or eliminating electrostatic charges on the surface of a silica-containing material, which remains effective and stable over a wide range of conditions and extended periods of time has now been discovered. In accordance with this method, a polymer coating is applied over the silica surface, the coating bonded to the surface through Si—C bonds without the intermediate siloxane moiety of the prior art. The method involves the placement of accessible ethenyl bonds at sites originally occupied by silanol groups, followed by an addition reaction across the ethenyl bond by an appropriate species for formation and covalent bonding of the polymer layer. The term "ethenyl bond" is used in this specification to denote the following:

Attachment of the accessible ethenyl bond is achieved by the use of an organometallic reagent bearing a terminal ethenyl moiety.

The bonds securing the polymer to the silica surface are stable over a wide range of pH, extending from strong acid to strong base, and remain stable for extended time periods. The resulting coating reduces or eliminates both electroosmotic flow and adsorption sites on the silica surface, providing the silica with broad versatility of use in terms of its application to different types of proteins, as well as high peak resolution and efficient separations.

Further features, objects and advantages of the invention will be apparent from the description which follows.

DETAILED DESCRIPTION OF THE INVENTION AND PREFERRED EMBODIMENTS

Figure 1A:
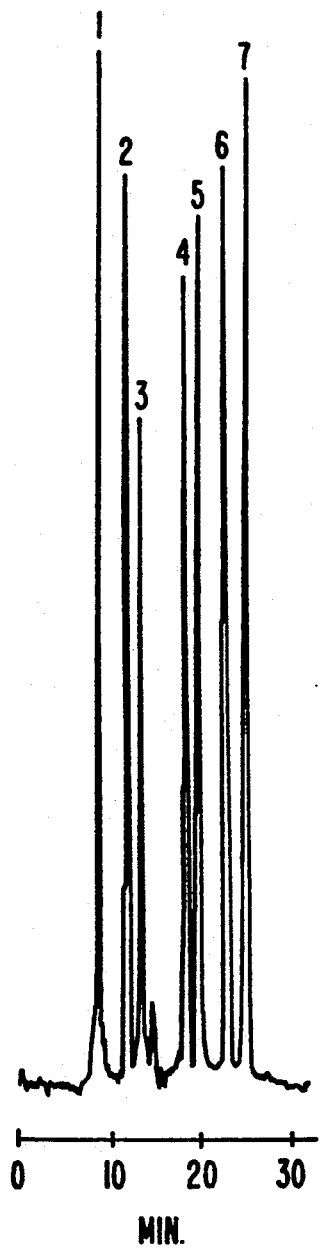
FIGS. 1a and 1b are detector traces representing electrophoretic separations performed in coated and uncoated capillaries in accordance with the invention, under high pH conditions.

In accordance with the invention, silanol groups on the surface of the silica-containing material are first converted to silicon halide groups to prepare them for reaction with the Grignard reagent. This may be achieved by conventional methods known to those skilled in the art. Halide atoms in general may be used. Chlorine and bromine are preferred, with chlorine particularly preferred.

A preferred method of chlorination is through the use of thionyl chloride. This reaction is generally performed in an inert atmosphere in the liquid phase at elevated temperature, preferably in excess of 50° C. While a solvent may be used, the reaction may also be performed in the absence of a solvent.

The halogenated surface sites are then treated with an organometallic agent bearing an aliphatic group with a terminal ethenyl moiety. Preferred organometallics are organolithium, organomagnesium and organosodium compounds. Organolithium and organomagnesium compounds are particularly preferred, and are of the general formulas R—Li and R—Mg—X, respectively.

In these formulas, R is an aliphatic group containing a terminal ethenyl moiety, and X is halogen. Preferred R groups are straight chain groups of 5 carbon atoms or less, with allyl and vinyl groups particularly preferred, and the vinyl group the most preferred. The X atom in the organomagnesium formula represents halogens in general. Chloride, bromide and iodide are the preferred halogens, chloride and bromide more preferred, and bromide the most preferred. Examples of preferred organometallic reagents are vinyl lithium, allyl lithium, vinyl magnesium bromide, vinyl magnesium chloride, allyl magnesium bromide and allyl magnesium chloride.

The reaction with the organometallic compound is likewise generally conducted under an inert dry atmosphere. The organometallic reagent is generally used in liquid solution in a polar solvent, notably an ether such as diethyl ether or tetrahydrofuran, and the reaction is generally conducted at elevated temperature, preferably about 50° C. or above.

The reaction with the organometallic reagent converts the silicon halide groups to Si—R groups, with the terminal ethenyl bond of the R group retained. The surface is then reacted with a species capable of addition polymerization at the ethenyl group to form a monomolecular polymer layer over the surface of the silica, and covalently bonded thereto at the sites formerly occupied by the silanol groups. The species used in this phase of the process may vary widely. Examples are acrylates, acrylamide, substituted acrylamides, and alkyl-, aryl- and halo-substituted ethylenes. Preferred among these are acrylates, acrylamide and substituted acrylamides, with acrylamide being the most preferred. In the case of acrylamide, the result is a monomolecular layer of noncrosslinked polyacrylamide.

The addition reaction is performed according to conventional techniques, employing reaction conditions and additional reagents known to those skilled in the art. The reaction is generally in the presence of a polymerization catalyst, which in the case of polyacrylamide is a base catalyst. Prime examples are amine bases such as N,N,N'N'-tetramethylethylenediamine ("TEMED" or "TMEDA"), β-dimethylaminopropionitrile and triethanolamine. In addition to the catalyst, a polymerization initiator is generally present. Notable examples of polymerization initiators are free radical initiators such as peroxides, persulfates or azo compounds. Example are benzoyl peroxide, tert-butyl peroxide, tert-butyl hydroperoxide, tert-butyl perbenzoate, cumyl peroxide, acetyl peroxide, lauroyl peroxide, 2,2'-azobisisobutyronitrile, phenyl-azo-triphenylmethane, and persulfates such as potassium persulfate and ammonium persulfate. A selection of the optimal catalyst and initiator in each case will depend on the species being reacted and possibly the reaction conditions. Conditions under which these reactions occur are generally known among those skilled in the art, and are equally applicable in this process.

The present invention is applicable to silica-containing surfaces in general. Examples are fused silica, glass and quartz. The invention is further applicable to a wide range of geometries, including slabs, tubes, beads, and other contours, shapes and size scales. As mentioned above, the invention is of particular interest as applied to capillaries, with a coating applied to the inner wall of the capillary. The dimensions of the capillary will vary according to choice, depending on the needs of the separation process itself. In most cases, the capillary will have an internal diameter ranging from about 5 microns to about 250 microns, preferably from about 20 microns to about 100 microns. Likewise, the length of the capillary will in most cases range from about 5 cm to about 500 cm, preferably from about 10 cm to about 100 cm.

Separation processes which can be conducted using the treated surface may vary widely as well. Capillaries treated in accordance with the invention are useful for electrophoretic processes in general, including both gel and liquid-phase electrophoresis, and are particularly useful in the separation of protein mixtures.

The following examples are offered for purposes of illustration, and are intended neither to define nor limit the invention in any manner.

EXAMPLE 1

Capillary Treatment Procedure

Reagents, solvents and capillaries

The proteins and buffer components, as well as the N,N,N',N'-tetramethylethylenediamine (TEMED), and electrophoresis-grade acrylamide were purchased from Sigma Chemical Co. (St. Louis, Mo., U.S.A.). Sources for the remaining reagents and solvents were as follows: reagent grade ammonium persulfate was purchased from Mallinkrodt Inc. (Paris, Ky., U.S.A.); vinyl magnesium bromide (1.0M in tetrahydrofuran) was purchased from Aldrich Chemical Co. (Milwaukee, Wis., U.S.A.); thionyl chloride (99%) was purchased from EM Science (Cherry Hill, N.J., U.S.A.) and distilled prior to use; and tetrahydrofuran (THF) was purchased from J. T. Baker, Inc. (Phillipsburg, N.J., U.S.A.) and dried over molecular sieve.

Distilled water was used in the preparation of buffers and all buffers were filtered through 0.2 $\mu$m Nylon 66 membrane filters (Alltech Associates, Deerfield, Ill., U.S.A.). Sample solutions were prepared by dissolving the proteins in water at concentrations of approximately 0.2 mg/mL.

Fused silica capillaries (50 $\mu$m i.d., approximately 1 m in length) were first rinsed with 1M NaOH for thirty minutes, followed by distilled water for thirty minutes. The capillaries were dried at 110° C. with a nitrogen purge overnight.

A. Surface Chlorination

A 2 mL vial of thionyl chloride was placed in a small pressurizing chamber which was subsequently flushed with nitrogen for fifteen minutes to remove all oxygen. One end of the capillary was then inserted in the chamber and nitrogen was passed through the capillary for several minutes. The inserted capillary end was then lowered into the thionyl chloride and a constant flow of nitrogen was passed through the chamber which was maintained in a sealed and pressurized state, thereby forcing thionyl chloride into the capillary. Once the capillary was filled with thionyl chloride, the capillary was sealed off at a point near the pressuring chamber, by use of a small propane torch. The opposite end of the capillary was then quickly attached to a vacuum apparatus and the capillary was evacuated and maintained at a vacuum of 60 millitorr or less for approximately twenty minutes, during which time the capillary was maintained at 60.C by immersion in a heating bath. The end of the capillary near the vacuum line connection was then sealed with a propane torch, and the sealed capillary was placed in a 70° C. heating bath for 12 hours.

B. Treatment with Grignard Reagent

A 10 mL vial under a nitrogen purge and fitted with a rubber septum was charged with 5 mL of dry THF. Nitrogen was bubbled through the THF in the vial for several minutes. Vinyl magnesium bromide (1 mL) was then added to the THF with a dry syringe, and the resulting solution was purged with nitrogen.

One end of the sealed, chlorinated capillary from Section A of this example was broken off with forceps while the capillary was immersed in dry THF. The open end thus formed was quickly placed in the vinyl magnesium bromide/THF solution. The other end of the capillary was then broken off and immediately connected to a vacuum line. The vinyl magnesium bromide/THF was thus drawn into the capillary by the vacuum. The solution was drawn through the capillary for several minutes, following which the end of the capillary in the solution was sealed off near the vial septum with a propane torch. The capillary was then placed in a 50° C. heating bath, and the vacuum (60 millitorr or less) was maintained for thirty minutes. The other end of the capillary was sealed near the vacuum line connection, and the sealed capillary was placed in a 70° C. heating bath for 12 hours.

C. Formation of Polyacrylamide Coating

The ends of the sealed capillary from Section B of this example were broken, and the thus opened capillary was rinsed with THF for several minutes. The THF was then removed, and the capillary was rinsed with distilled water for several minutes, following which the water was removed.

An acrylamide solution was prepared by mixing 0.3 mL of 10% acrylamide, 0.7 mL water, 1 $\mu$L TEMED, and 10 $\mu$L of 10% ammonium persulfate, and deaerating the resulting mixture. The capillary was then filled with the solution. After thirty minutes, excess acrylamide was rinsed from the capillary with water, leaving a chemically bonded layer of acrylamide (polymerized, but not crosslinked) on the inner walls of the capillary.

D. Reproducibility of Treatment

Five capillaries were coated with polyacrylamide in the manner described above. Each was then tested with α-lactalbumin under the following conditions:
buffer: 0.05M glutamine, triethylamine (pH 9.5);
capillary: 50 $\mu$m i.d. × 60cm (45 cm to detector);
injection: hydrodynamic; 5 sec with 20 cm height differential;
applied field: 20 kV, 15 $\mu$A, polarity negative (cathode at injection end).

The number of theoretical plates was determined for each run, using the formula $$N = \frac{(\text{first moment})^2}{\text{second moment}}$$

where N is the number of theoretical plates. Relative standard deviations were then determined for both migration times and the number of theoretical plates, and both were less than 5% for the coated capillaries. For the uncoated capillaries, the relative standard deviations were both under 3%.

Examples 2 and 3 demonstrate the use of capillaries prepared according to the procedure of Example 1, and comparisons of these capillaries with uncoated capillaries. The equipment and methods used in Examples 2 and 3 is as follows.

A high voltage power supply (0–30 kV), purchased from Spellman High Voltage Electronics Corporation (Plainview, N.J., U.S.A.), was used. Detection was performed with a variable wavelength UV-absorbance detector (UVIDEC-100-V, Jasco, Tokyo, Japan), operated at 214 nm. The capillaries used were fused silica capillaries (Polymicro Technologies, Phoenix Ariz., U.S.A.) with an inner diameter of 50 μm and an outer diameter of 187 μm. An optical window was formed in each capillary by removing a small section of the polyacrylamide coating. The samples were about 1.2 nL in volume, which corresponded to approximately 240 pg of an individual protein. The samples were introduced by hydrodynamic flow, and sample volumes were calculated using the known injection times and the measured velocity of hydrodynamic flow, as described by Rose, D. J., et al., *J. Chromatogr.* 438:23–34 (1988).

Uncoated capillaries were rinsed sequentially with 0.1M NaOH and buffer for approximately 2 minutes each between runs, while the coated capillaries were rinsed with buffer only between runs. Tests for electroosmotic flow were conducted by the use of acetone (2% aqueous solution) as a neutral marker. Such tests were conducted at least two times per day, or as deemed necessary when following the effects of various buffer systems on the capillary coating. Data collection and processing were performed on an IBM personal computer.

EXAMPLE 2

High pH Protein Separations

A. Effect of Wall Treatment on Resolution

Separations were performed on the following protein mixture at pH 9.5, using both uncoated capillaries and capillaries coated in accordance with the present invention:

TABLE 1

Sample Mixture for FIG. 1

| Protein | Molecular Weight | Isoelectric Point |
|---|---|---|
| 1. Insulin Chain A (Porcine) | 2,500 | 4.3 |
| 2. Serum Albumin (Bovine) | 66,000 | 4.7 |
| 3. Ovalbumin (Chicken Egg) | 45,000 | 4.7 |
| 4. Insulin (Porcine) | 6,000 | 5.4 |
| 5. α-Lactalbumin (Bovine Milk) | 14,200 | 4.8 |
| 6. β-Casein (Bovine Milk) | 24,000 | 4.5 |
| 7. Insulin Chain B (Porcine) | 3,500 | 7.6 |

The conditions for separation were as follows:
buffer: 0.05M glutamine, triethylamine (pH 9.5);
capillary: 50 μm i.d.×60 cm (45 cm to detector);
injection: hydrodynamic; 5 sec with 20 cm height differential;
applied field: coated capillaries: 20 kV, 15 μA, polarity negative (cathode at injection end); uncoated capillaries: 10 kV, 7 μA, polarity positive (anode at injection end).

Note that the applied voltage used for the runs with coated capillaries were significantly higher than those used with uncoated capillaries. Since there was no electroosmotic flow in the coated capillary runs, the higher voltage served to promote faster migration of the proteins through the capillary toward the cathode. In the uncoated capillaries, strong electroosmotic flow occurred in the direction of the cathode and was the dominant migratory force on the sample ions, while the electrophoretic force was in the opposite direction, serving to separate the ions and achieve what limited peak resolution could be obtained. The result was an optimized separation in each case.

Figure 1B:
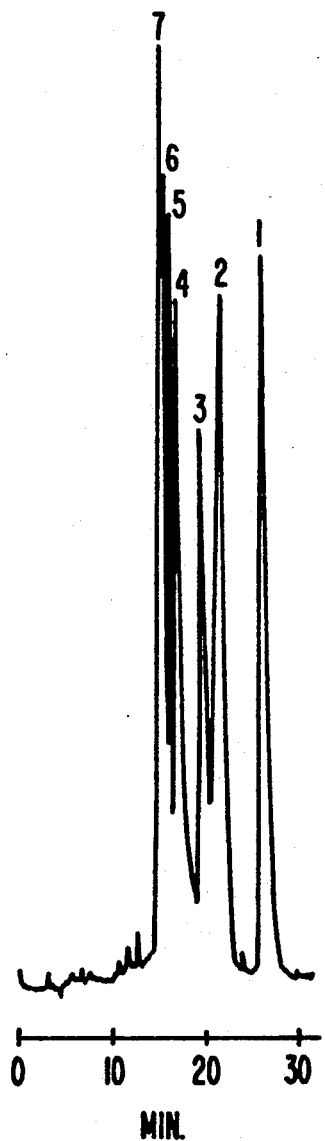

The results are shown in FIG. 1, which shows a typical detector trace obtained using a coated capillary in FIG. 1a, and one obtained using an uncoated capillary in FIG. 1b, under the conditions described above. The identity of the protein represented by each peak is indicated by number in conformance with Table 1 above. It is clear from a comparison of the two traces that the coated capillary provides a significantly improved separation.

B. Effect of Wall Treatment on Migration Time Reproducibility

Using five runs each for both the coated and uncoated capillaries, the relative standard deviation of the migration time of each of the proteins was determined. The results are listed in Table 2 below.

TABLE 2

Migration Time Standard Deviations

| Protein | % Relative Standard Deviation (n = 5) | |
|---|---|---|
| | Coated Capillary | Uncoated Capillary |
| Insulin Chain A (Porcine) | 0.11 | 3.51 |
| Serum Albumin (Bovine) | 0.18 | 2.69 |
| Ovalbumin (Chicken Egg) | 0.19 | 3.03 |
| Insulin (Porcine) | 0.12 | 2.23 |
| α-Lactalbumin (Bovine Milk) | 0.32 | 2.56 |
| β-Casein (Bovine Milk) | 0.25 | 1.93 |
| Insulin Chain B (Porcine) | 0.20 | 1.64 |

As the data in Table 2 indicate, coating of the capillary in accordance with this invention results in an improvement in the reproducibility by approximately an order of magnitude, which is attributable to the effects that electroosmotic flow and analyte adsorption have on migration times.

To confirm the absence of electroosmotic flow in the coated capillary, electroosmotic flow tests using acetone as a neutral marker were performed as described in Example 1 above. In a test conducted after three hours of exposure to the alkaline conditions, with the power supply at a positive polarity of 20 kV, the neutral marker failed to appear at the detector. The electroosmotic flow coefficient in $m^2$/V-sec may be determined by the following equation, per Jorgenson, J. W., et al., *J. Chromatogr.* 53:1298–1302 (1981):

$$\mu_{eo} = \frac{L_{tot} \cdot L_{sep}}{V \cdot t_o}$$

where
$\mu_{eo}$ = electroosmotic flow coefficient
$L_{tot}$ = total capillary length
$L_{sep}$ = capillary length from injection end to detector
$V$ = applied voltage
$t_o$ = migration time of the neutral marker Applying this equation, the electroosmotic flow measured in the coated capillary after three hours was less than $1.25 \times 10^{-9} m^2$/V-sec, while that occurring in the uncoated capillary was $5.4 \times 10^{-8} m^2$/V-sec.

C. Effect of Wall Treatment on Separation Efficiency and Peak Shape

Theoretical plate count and peak skew for both the coated and uncoated capillaries were determined using α-lactalbumin and bovine albumin. Calculations for these parameters were performed in accordance with the methods disclosed by Kirkland, J. J., et al., *J. Chromatogr. Sci.* 15:303–316 (1977), as follows (N=number of theoretical plates):

$$N = \frac{(\text{first moment})^2}{\text{second moment}}$$

$$\text{peak skew} = \frac{\text{third moment}}{(\text{second moment})^{3/2}}$$

The results are listed in Table 3:

TABLE 3
Theoretical Plate Count and Peak Skew for Proteins Separated at pH 9.5

| Protein | Voltage (kV) | Current (μA) | Theoretical Plates Per meter Coated | Theoretical Plates Per meter Uncoated | Peak Skew[a] Coated | Peak Skew[a] Uncoated |
|---|---|---|---|---|---|---|
| α-Lactalbumin | 10 | 7 | 293,000 | 71,000 | 0.049 | 0.939 |
|  | 15 | 11 | 251,000 | 59,000 | 0.061 | 0.996 |
|  | 20 | 15 | 216,000 | 42,000 | 0.077 | 1.075 |
|  | 25 | 21 | 194,000 | 39,000 | 0.079 | 1.101 |
| Bovine Albumin | 10 | 7 | 259,000 | 69,000 | 0.059 | 1.018 |
|  | 15 | 11 | 233,000 | 56,000 | 0.078 | 1.024 |
|  | 20 | 15 | 209,000 | 48,000 | 0.081 | 1.108 |
|  | 25 | 21 | 107,000 | 42,000 | 0.087 | 1.117 |

[a]Peak skew values ranging from 0 to 0.002 indicate perfect Gaussian peaks. Peak skew values in excess of 1.0 indicate moderate to severe tailing.

The data in Table 3 indicate that the coated capillary performed in a manner superior to the uncoated capillary in terms of both the number of theoretical plates and the peak skew. In particular, the values for peak skew in the coated capillary indicate very little tailing. This indicates that any protein adsorption which is occurring is reversible and equilibration occurs at a rapid rate.

The buffer used in generating the data listed in FIG. 2 was the glutamine/triethylamine buffer referred to above. To investigate possible effects of buffer components on efficiencies, a borate buffer (0.05M sodium borate, pH 9.5) was used in place of the glutamine/triethylamine buffer in parallel tests. The borate buffer yielded N and peak skew values which were very similar to or slightly improved over those obtained with the glutamine/triethylamine buffer, although resolution with the borate buffer was less satisfactory. The similarity in N and peak skew are an indication that protein interactions with buffer components are not a likely cause of peak broadening. It also indicates that the triethylamine does not act to mask residual silanol groups of the coated capillary, and that the reduction in capillary surface charge is indeed a result of the polymer coating.

D. Long-Term Stability

After four weeks of continual use with pH 9.5 buffers (buffer replaced with water overnight), including more than 150 injections, electroosmotic flow tests indicated that electroosmotic flow had not returned to a measurable extent, and protein migration times remained consistent from day to day, with less than 2% relative standard deviation for a five-day period. This indicated that the coating material had remained intact and the capillary walls had maintained their neutral character over this time.

In addition, the capillary walls were exposed to pH 10.5 buffers for five days, with no evidence of deterioration of the capillary coating. Deterioration of the coating was induced however by retention of a pH 11 buffer in the capillary for two days, after which time an electroosmotic flow test indicated an electroosmotic flow coefficient of $6.8 \times 10^{-9}$ m²/V-sec. This value, while still considerably less than that measured for an uncoated capillary, is an indication that the polyacrylamide coating had been partially removed to expose free silanol groups on the capillary surface.

EXAMPLE 3
Low pH Protein Separations
A. Effect of Wall Treatment on Resolution Low pH separations are particularly useful when dealing with very basic proteins, such as those with isoelectric points greater than 10.0. The separation of such proteins as anions would require a buffer at a pH in the range of 11–12. This is not practical in terms of capillary stability, or in many cases in terms of the stability of the sample components as well. At low pH, however, the proteins can acquire a positive charge and migrate toward the cathode.

To test separations of basic proteins at low pH, the following protein mixture was used:

TABLE 4
Sample Mixture for FIG. 2

| Protein | Molecular Weight | Isoelectric Point |
|---|---|---|
| 11. Cytochrome c (Horse Heart) | 12,400 | 10.7 |
| 12. Lysozyme (Chicken Egg White) | 14,100 | 11.1 |
| 13. Trypsin (Bovine Pancreas) | 24,000 | 10.1 |
| 14. Trypsinogen (Bovine Pancreas) | 23,700 | 8.7 |
| 15. Trypsin Inhibitor (Soybean) | 20,100 | 4.5 |

The conditions for separation were as follows:
buffer: 0 03M citric acid (pH 2.7, adjusted with 1M NaOH);
capillary: 50 μm i.d.×60 cm (45 cm to detector);
injection: hydrodynamic; 5 sec with 20 cm height differential;
applied field: coated capillaries: 20 kV, 10 μA; uncoated capillaries: 12 kV, 5 μA, polarity positive in both cases.

As in the high pH experiments, a higher voltage was used for the coated capillary to accelerate the separation.

Figure 2A:
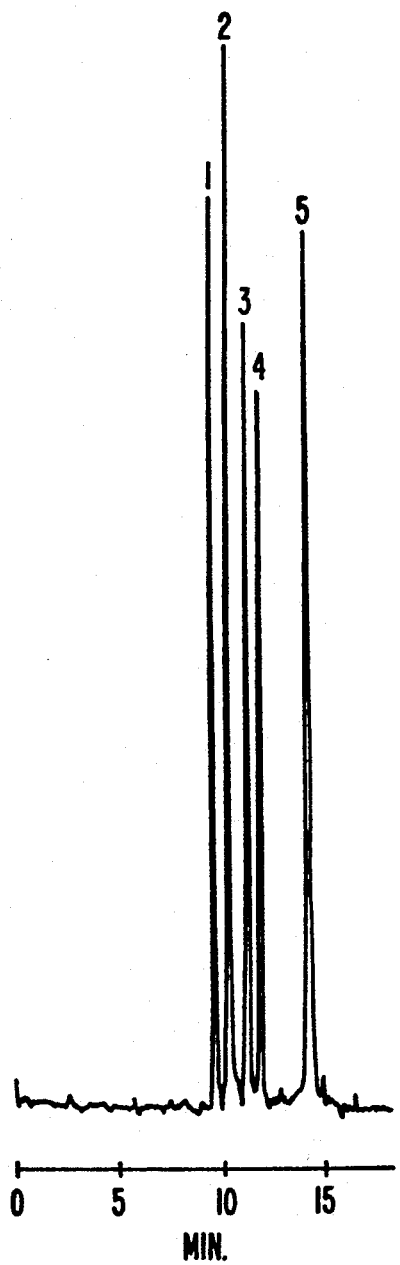
FIGS. 2a and 2b are detector traces similar to those of FIGS. 1a and 1b, using however a different protein mixture and conducted under low pH conditions.
Figure 2B:
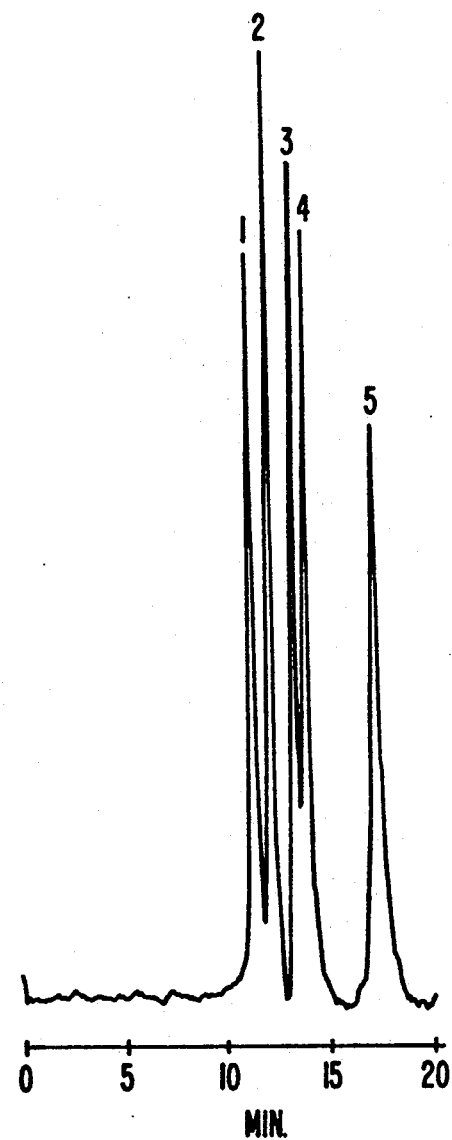

The results are shown in FIG. 2, which shows a typical detector trace obtained using a coated capillary in FIG. 2a, and one obtained using an uncoated capillary in FIG. 2b, under the conditions described above. The identity of the protein represented by each peak is indicated by number in conformance with Table 4 above.

It is clear from a comparison of the two traces that the coated capillary provides a significantly improved separation under low pH conditions as well as high pH. Again, no electroosmotic flow was detectable in the coated capillary.

The electroosmotic flow coefficient in the uncoated capillary, calculated in accordance with the formula given above, was $2.4 \times 10^{-8} m^2/V\text{-sec}$, which was approximately two times slower than that occurring in the uncoated capillary of Example 2 above at pH 9.5. In spite of this reduced electroosmotic flow, and a longer separation time, the resolution in the uncoated capillary was still inferior to that obtained in the coated capillary. In addition, the improved peak shape obtained with the coated capillary indicated reduced electrostatic interaction of proteins with the coated capillary walls.

B. Effect of Wall Treatment on Migration Time Reproducibility

Using five runs each for both the coated and uncoated capillaries, the relative standard deviation of the migration time of each of the proteins was determined. The results are listed in Table 5 below.

TABLE 5

Migration Time Standard Deviations

| Protein | % Relative Standard Deviation (n = 5) | |
|---|---|---|
| | Coated Capillary | Uncoated Capillary |
| Cytochrome c (Horse Heart) | 0.21 | 1.84 |
| Lysozyme (Chicken Egg White) | 0.24 | 2.13 |
| Trypsin (Bovine Pancreas) | 0.28 | 2.36 |
| Trypsinogen (Bovine Pancreas) | 0.31 | 2.84 |
| Trypsin Inhibitor (Soybean) | 0.25 | 3.12 |

Here again, the data in the table indicates that coating of the capillary in accordance with this invention results in an improvement in the reproducibility by approximately an order of magnitude.

C. Effect of Wall Treatment on Separation Efficiency and Peak Shape

Theoretical plate count and peak skew for both the coated and uncoated capillaries were determined using cytochrome c and trypsinogen.

The results are listed in Table 6:

TABLE 6

Theoretical Plate Count and Peak Skew for Proteins Separated at pH 9.5

| Protein | Voltage (kV) | Current (μA) | Theoretical Plates Per meter | | Peak Skew | |
|---|---|---|---|---|---|---|
| | | | Coated | Uncoated | Coated | Uncoated |
| Cytochrome c | 10 | 4 | 317,000 | 76,000 | 0.041 | 1.006 |
| | 15 | 6 | 298,000 | 62,000 | 0.057 | 1.027 |
| | 20 | 9 | 235,000 | 54,000 | 0.071 | 1.116 |
| | 25 | 12 | 194,000 | 51,000 | 0.077 | 1.127 |
| Trypsinogen | 10 | 4 | 297,000 | 73,000 | 0.035 | 0.904 |
| | 15 | 6 | 276,000 | 63,000 | 0.049 | 0.930 |
| | 20 | 9 | 220,000 | 59,000 | 0.063 | 1.018 |
| | 25 | 12 | 187,000 | 55,000 | 0.079 | 1.079 |

The data in Table 6 indicate here again, a much greater number of theoretical plates are observed in the coated capillary than in the uncoated capillary, and the values for peak skew in the coated capillary indicate only slight tailing, as compared to significant tailing in the uncoated capillary.

D. Long-Term Stability

A coated capillary was used for two weeks at pH 2.7 with no indication of deterioration, as detectable by daily electroosmotic flow tests. The capillary was then used at pH 2.0 for one week, with no measurable electroosmotic flow. The best separations were obtained at pH 2.7.

The foregoing is offered primarily for purposes of illustration. It will be readily apparent to those skilled in the art that variations, substitutions, and modifications in general may be made in terms of both materials and procedures without departing from the spirit and scope of the invention.

What is claimed is:

1. A method for separating a protein mixture in a liquid sample into components, said method comprising passing said sample through an electrophoretic medium under conditions promoting differential rates of migration of said protein therein, said electrophoretic medium retained in an enclosure formed of a silica-containing material coated with a layer of a non-silicon-containing uncharged organic polymer covalently bonded to said silica-containing material by bonds joining Si atoms of said silica-containing material directly to C atoms of said polymer.

2. A method in accordance with claim 1 in which said silica-containing material is fused silica.

3. A method in accordance with claim 1 in which said polymer is polyacrylamide.

4. A method in accordance with claim 1 in which said electrophoretic medium is an aqueous solution.

5. A method in accordance with claim 1 in which said enclosure is a capillary.

6. A method for separating a protein mixture in a liquid sample into components, said method comprising passing said sample through a capillary of silica-containing material under conditions promoting an electrophoretic separation of said proteins in said capillary, the inner wall of said capillary coated with a layer of polyacrylamide covalently bonded to said silica-containing material by bonds joining Si atoms of said capillary directly to C atoms of said polyacrylamide.

* * * * *